(12) United States Patent
Young et al.

(10) Patent No.: US 9,211,277 B2
(45) Date of Patent: Dec. 15, 2015

(54) DIETARY SUPPLEMENT COMPOSITION

(71) Applicant: Young Living Essential Oils, LC, Lehi, UT (US)

(72) Inventors: D. Gary Young, Alpine, UT (US); Marc Schreuder, Provo, UT (US)

(73) Assignee: Young Living Essential Oils, LC, Lehi, UT (US)

(*) Notice: Subject to any disclaimer, the term of this patent is extended or adjusted under 35 U.S.C. 154(b) by 0 days.

(21) Appl. No.: 13/786,708

(22) Filed: Mar. 6, 2013

(65) Prior Publication Data

US 2014/0255370 A1 Sep. 11, 2014

Related U.S. Application Data

(60) Provisional application No. 61/761,912, filed on Feb. 7, 2013.

(51) Int. Cl.

| | |
|---|---|
| *A61K 31/122* | (2006.01) |
| *A61K 31/355* | (2006.01) |
| *A61K 31/202* | (2006.01) |
| *A61K 31/592* | (2006.01) |
| *A61K 31/593* | (2006.01) |
| *A61K 35/60* | (2006.01) |
| *A23L 1/30* | (2006.01) |
| *A23L 1/302* | (2006.01) |
| *A61K 36/00* | (2006.01) |

(52) U.S. Cl.
CPC ............. *A61K 31/355* (2013.01); *A23L 1/30* (2013.01); *A23L 1/302* (2013.01); *A23L 1/3006* (2013.01); *A61K 31/122* (2013.01); *A61K 31/202* (2013.01); *A61K 31/592* (2013.01); *A61K 31/593* (2013.01); *A61K 35/60* (2013.01); *A61K 36/00* (2013.01)

(58) Field of Classification Search
None
See application file for complete search history.

(56) References Cited

U.S. PATENT DOCUMENTS

| | | | | |
|---|---|---|---|---|
| 5,955,102 | A * | 9/1999 | Gorenbein et al. | 424/451 |
| 8,389,504 | B2 | 3/2013 | Debbouz et al. | |
| 2008/0213236 | A1 | 9/2008 | Flavin-Koenig | |
| 2008/0319071 | A1* | 12/2008 | Raederstorff et al. | 514/559 |
| 2009/0061048 | A1* | 3/2009 | Kohane et al. | 426/62 |
| 2009/0175936 | A1* | 7/2009 | Rohr | 424/464 |
| 2009/0186096 | A1* | 7/2009 | Kritzman et al. | 424/523 |
| 2009/0317532 | A1* | 12/2009 | Bromley | 426/590 |
| 2010/0178369 | A1* | 7/2010 | Arledge et al. | 424/766 |

FOREIGN PATENT DOCUMENTS

| | | |
|---|---|---|
| DE | 202007007584 U1 * | 9/2007 |
| WO | 8902275 | 3/1989 |
| WO | 9962356 | 12/1999 |
| WO | WO 2008009615 A1 * | 1/2008 |
| WO | 2010096564 | 8/2010 |

OTHER PUBLICATIONS

Stoll, Andrew L., "Omega 3 Fatty Acids in Bipolar Disorder", Arch Gen Psychiatry, May 1999, pp. 6, vol. 56, www.archgenpsychiatry.com.
Roberts, W. G., "Effects of Enhanced Consumption of Fruit and Vegetables on Plasma Antioxidant Status and Oxidative Resistance of LDL in Smokers Supplemented with Fish Oil", European Journal of Clinical Nutrition, 2003, pp. 9, www.nature.com/ejcn.
Miller III, Edgar R., "Meta-Analysis: High-Dosage Vitamin E Supplementation May Increase All-Cause Mortality", Annals of Internal Medicine, Jan. 4, 2005, pp. 11, vol. 142, No. 1, www.annals.org.
Nagashima, Kiyoshi, "Inhibitory Effect of Eugenol on Cu2+ -Catalyzed Lipid Peroxidation in Human Erythrocyte Membranes", Int. J. Biochem., 1989, pp. 6, vol. 21, No. 7 pp. 745-749, Great Britain.
Recsan, Zsuzsa, "Effect of Essential Oils on the Lipids of the Retina in the Ageing Rat: A Possible Therapeutic Use", Journal of Essential Oil Research, 1997, pp. 6, 9:1, 53-56, http://dx.doi.org/10.1080/10412905.1997.9700714.
Yu, Weiping, "Induction of Apoptosis in Human Breast Cancer Cells by Tocopherols and Tocotrienols", Nutrition and Cancer, 1999, pp. 6, vol. 33(1), pp. 26-32.
Teissedre, P. L, "Inhibition of Oxidation of Human Low-Density Lipoproteins by Phenolic Substances in Different Essential Oils Varieties", J. Agric. Food Chem., 2000, pp. 6, vol. 48, pp. 3801-3805.
Fritsche, Kevin L., "Rapid Autoxidation of Fish Oil in Diets without Added Antioxidants1", The Journal of Nutrition, Dec. 3, 1987, pp. 2.
Calder, Philip C., "Omega-3 Polyunsaturated Fatty Acids and Inflammatory Processes: Nutrition or Pharmacology?" British Journal of Clinical Pharmacology, 2012, pp. 43.
Manson, J., "The VITamin D and OmegaA-3 Trial (VITAL): Rationale and Design of a Large Randomized Controlled Trial of Vitamin D and Marine Omega-3 Fatty Acid Supplements for the Primary Prevention of Cancer and Cardiovascular Disease", Contemporary Clinical Trials, Apr. 22, 2011, pp. 14, vol. 33, pp. 159-171, journal homepage: www. elsevier.com/locate/conclintrial.
Rizos, Evangelos C., "Association Between Omega-3 Fatty Acid Supplementation and Risk of Major Cardiovascular Disease Events", JAMA, Sep. 12, 2012, pp. 10, vol. 308, No. 10, http://jama.jamanetwork.com/ onMar. 7, 2013.
Song, Jin Hyang, "Polyunsaturated (n-3) Fatty Acids Susceptible to Peroxidation Are Increased in Plasma and Tissue Lipids of Rats Fed Docosahexaenoic Acid-Containing Oils", American Society for Nutritional Sciences, Jul. 31, 2000, pp. 6.

(Continued)

*Primary Examiner* — Blaine Lankford
*Assistant Examiner* — David Berke-Schlessel
(74) *Attorney, Agent, or Firm* — Kunzler Law Group, PC

(57) ABSTRACT

A dietary supplement composition is presented, which includes omega-3 fatty acids, one or more of tocopherols and tocotrienols, and/or one or more essential oils. The dietary supplement may provide numerous health benefits to the user, including improvements in cardiovascular health, ocular health, cerebral and cognitive function, muscle function, and athletic performance. This supplement also has pronounced anti-inflammatory benefits. The collective effect of the composition may also maximize the positive effects of omega-3 fatty acids while also reducing or eliminating any negative effects associated with these fats.

20 Claims, No Drawings

(56) References Cited

OTHER PUBLICATIONS

Makpol, Suzana, "Gamma-tocotrienol Modulation of Senescence-associated Gene Expression Prevents Cellular Aging in Human Diploid Fibroblasts", CLINICS, Sep. 8, 2011, pp. 9, http://creativecommons.org/licenses/by-nc/3.0/.
Hill, Alison M., "Combining Fish-Oil Supplements with Regular Aerobic Exercise Improves Body Composition and Cardiovascular Disease Risk Factors", American Society for Nutrition, 2007, pp. 8, vol. 85, pp. 1267-1274.
Papadimitropoulos, Emmanuel, "VIII: Meta-Analysis of the Efficacy of Vitamin D Treatment in Preventing Osteoporosis in Postmenopausal Women", The Endocrine Society, 2002, pp. 10, vol. 23(4), pp. 560-569.
Harris, Susan S., "Vitamin D Insufficiency and Hyperparathyroidism in a Low Income, Multiracial, Elderly Population*", The Journal of Clinical Endocrinology & Metabolism, 2000, pp. 6, vol. 85, No. 11.
Nesaretnam, Kalanithi, "Tocotrienol-Rich Fraction from Palm Oil and Gene Expression in Human Breast Cancer Cells", Annals New York Academy of Sciences, 2004, pp. 15, vol. 1031, pp. 143-157.
Ortega, R. M., "Effects of Omega 3 Fatty Acids Supplementation in Behavior and Non-Neurodegenerative Neuropsychiatric Disorders", British Journal of Nutrition, 2012, pp. 10.
Earthman, C. P., "The Link Between Obesity and Low Circulating 25-Hydroxyvitamin D Concentrations: Considerations and Implications", International Journal of Obesity, 2012, pp. 10, vol. 36, pp. 387-396, www.nature.com/ijo.
Ghosh, Sanchita P., "Gamma-tocotrienol, a Tocol Antioxidant as a Potent Radioprotector", Informa Healthcare, Jul. 2009, pp. 10, Int. J. Radiat. Biol., vol. 85, No. 7, pp. 598-606.
Freeman, Marlene P., "Omega-3 Fatty Acids: Evidence Basis for Treatment and Future Research in Psychiatry", J. Clin. Psychiatry, Dec. 2006, pp. 14, vol. 67:12.
Nesaretnam, Kalanithi, "Effect of Tocotrienols on Growth of a Human Breast Cancer Cell Line in Culture", Lipids, 1995, pp. 6, vol. 30, Issue 12, pp. 1139-1143.
Li, Jing-Jing, "Anti-Obesity Effects of Conjugated Linoleic Acid, Docosahexaenoic Acid, and Eicosapentaenoic Acid", WILEY-VCH Verlag GmbH & Co., 2008, pp. 15, Mol. Nutr. Food Res. vol. 52, pp. 631-645.
Kulkarni, Shilpa, "Gamma-Tocotrienol Protects Hematopoietic Stem and Progenitor Cells in Mice after Total-Body Irradiation", BioOne, 2010, pp. 11, Radiation Research Society, vol. 173(6), pp. 738-747.
Kabadi, Shaum M., "Joint Effects of Obesity and Vitamin D Insufficiency on Insulin Resistance and Type 2 Diabetes", Diabetes Care, Oct. 2012, pp. 7, vol. 35, http://creativecommons.org/licenses/by-nc-nd/3.0/.
Lee, Kwang-Geun, "Determination of Antioxidant Potential of Volatile Extracts Isolated from Various Herbs and Spices", Journal of Agricultural and Food Chemistry, 2002, pp. 7, vol. 50, pp. 4947-4952.
"Omega Blue", Young Living Essential Oils, 2008, pp. 2, www.youngliving.com.
Campbell, Sharon E., "γ-Tocotrienol Induces Growth Arrest Through a Novel Pathway with TGFB2 in Prostate Cancer", Elsevier, Inc., 2011, pp. 11, www.elsevier,com/locate/freeradbiomed.
Vasickova, Ludmila, "Possible Effect of DHA Intake on Body Weight Reduction and Lipid Metabolism in Obese Children", Neuroendocrinolgy Letters, Oct. 11, 2011, pp. 4, vol. 32, Suppl. 2.
Carrillo, Andres E., "Impact of Vitamin D Supplementation During a Resistance Training Intervention on Body Composition, Muscle Function, and Glucose Tolerance in Overweight and Obese Adults", Clinical Nutrition, 2012, pp. 7, http://dx.doi.org/10.1016/j.cinu.2012.08.014.
Leblanc, Erin S., "Associations Between 25-Hydroxyvitamin D and Weight Gain in Elderly Women", Journal of Women's Health, 2012, pp. 8, vol. 21, No. 10.
Young Living Essential Oils, Omega Blue Product Information Page, 2008, youngliving.com, USA.
Zsuzsa et al., Effect of Essential Oils on the Lipids of the Retina in the Ageing Rat: A Possible Therapeutic Use, Journal of Essential Oil Research, Jan./Feb. 1997, 53-56, 9, 1.
Kevin L. Fritsche and Patricial V. Johnston, Rapid Autoxidation of Fish Oil in Diets without Added Antioxidants, The Journal of Nutrition, 1988, 425-426.
Manson et al, Contemporary Clinical Trials: Vitamini D and Omega-3 Trial, Elsevier, Jan. 2012, 159-171, Oct. 2.

* cited by examiner

DIETARY SUPPLEMENT COMPOSITION

RELATED APPLICATIONS

This application claims the benefit of U.S. Provisional Application No. 61/761,912, filed Feb. 7, 2013, entitled A DIETARY SUPPLEMENT COMPOSITION, which is incorporated herein by reference in its entirety.

BACKGROUND

Omega-3 fatty acids are believed to be vital nutrients for promoting brain health, eye structure, and cardiovascular health. These fatty acids have been shown to reduce systemic inflammation in the human body that increases with age. These age-related, pro-inflammatory effects may contribute to many chronic diseases associated with aging, including arthritis, digestive disturbances, and even cancer. Some research also suggests that omega-3 fats are prone to oxidation or peroxidation which can result in their having deleterious effects on health and result in negative side-effects.

SUMMARY

The present invention relates to a dietary supplements composition that may provide the positive effects of omega-3 fatty acids while also avoiding or eliminating any negative effects associated with these fats. This novel dietary supplement that may provide substantial health benefits to individuals who consume this supplement on a periodic or regular basis. The present composition includes one or more of omega-3 fatty acids, one or more mixed or tocopherols or tocotrienols, one or more essential oils, vitamin D2 and/or vitamin D3, coenzyme Q10 (CoQ10), and/or mixed carotenoids. The synergistic effect of the combination of these components in a composition can maximize the stability of composition and/or improve the convenience of the dietary supplement for the user.

One aspect of the invention relates a dietary supplement composition that includes omega-3 fatty acids in an amount of at least about 20 percent by weight, one or more tocopherols and/or tocotrienols, and one or more essential oils in an amount of at least about 0.5 percent by weight. Another aspect of the invention relates to a dietary supplement composition that includes omega-3 fatty acids in an amount of at least 20 percent by weight, at least one of vitamin D2 and vitamin D3, coenzyme Q10 (CoQ10), and one or more essential oils. Yet another aspect of the invention relates to a dietary supplement composition that includes omega-3 fatty acids in an amount of at least about 30% by weight, coenzyme Q10 (CoQ10), at least one of vitamin D2 and vitamin D3, one or more tocopherols and/or tocotrienol, and one or more essential oils in an amount of at least about 1% by weight.

DETAILED DESCRIPTION OF EXEMPLARY EMBODIMENTS

This specification describes exemplary embodiments and applications of the invention. The invention, however, is not limited to these exemplary embodiments and applications or to the manner in which the exemplary embodiments and applications operate or are described herein. Where reference is made to a list of elements (e.g., elements a, b, c), such reference is intended to include any one of the listed elements by itself, any combination of less than all of the listed elements, and/or a combination of all of the listed elements.

Numerical data may be expressed or presented herein in a range format. It is to be understood that such a range format is used merely for convenience and brevity and thus should be interpreted flexibly to include not only the numerical values explicitly recited as the limits of the range, but also as including all the individual numerical values or sub-ranges encompassed within that range as if each numerical value and sub-range is explicitly recited. As an illustration, a numerical range of "about 1 to 5" should be interpreted to include not only the explicitly recited values of about 1 to 5, but also include individual values and sub-ranges within the indicated range. Thus, included in this numerical range are individual values such as 2, 3, and 4 and sub-ranges such as 1-3, 2-4, and 3-5, etc. This same principle applies to ranges reciting only one numerical value and should apply regardless of the breadth of the range or the characteristics being described.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The present invention relates generally to a dietary supplement composition (herein simply "composition"). In some aspects, the composition includes omega-3 fatty acids, one or more tocopherols and/or tocotrienols, and one or more essential oils, with some embodiments of the composition further including one or more of coenzyme Q10 (CoQ10), vitamin D2, vitamin D3, and one or more mixed carotenoid. Other aspects of the invention include omega-3 fatty acids, coenzyme Q10 (CoQ10), vitamin D2 and/or D3, and one or more essential oils, with some embodiments further including one or more tocopherols and/or tocotrienols.

In some instances, the synergistic effect of the combination of the components in the composition maximizes the stability of composition and/or improves the convenience of the dietary supplement for the user. Moreover, the composition may further include a fish gelatin capsule into which the other components of the composition may be included for administration to a human user. Each of these components will now be individually described in detail.

In some embodiments, each of the components of the composition is oil soluble, thus eliminating the need for emulsification, which may provide stability to the composition, convenience to the user, and improve the ability of the composition to be absorbed by the body when consumed. By mixing these oil-soluble components together they become completely miscible without the need for homogenization, additives or other types of emulsifiers or emulsification techniques—all which would be required if water soluble or aqueous-type nutrients were to be combined with the oil or lipid-soluble ingredients.

As mentioned, embodiments of the composition can include one or more omega-3 fatty acids. Such fatty acids are believed to include a number of health benefits when consumed by humans, including support for brain, heart, eye, and joint health. Omega-3 fatty acids are fats commonly found in marine and plant oils. They are polyunsaturated fatty acids with a double bond (C=C) starting after the third carbon atom from the end of the carbon chain. The fatty acids have two ends—the acid (COOH) end and the methyl ($CH_3$) end. The location of the first double bond is counted from the methyl end. Examples of omega-3 fatty acids, which can be included in the composition, include α-Linolenic acid (ALA), Eicosapentaenoic acid (EPA), Docosahexaenoic acid (DHA), which can be included individually or in combination. Omega-3 fatty acids included in the composition can be originally found in fish oils (e.g., cod liver oil), squid oils, krill oil, and plant oils (such as oil from walnuts or flaxseed oil). Accordingly, in some embodiments, the composition includes one or more fish oil, squid oil, krill oil, or plant oil. Additionally or alternatively, the composition may include ALA, EPA, and/or DHA isolated, extracted, or otherwise separated from one or more fish oil, squid oil, krill oil, or plant oil In some embodiments, the composition may include one or more omega-3 fatty acids in amounts between about 0.1 milligram (mg) to 5 grams (g), between about 1 mg to 5 g, between about 10 mg to 4 g, between about 50 mg to 3.5 g, between about 50 mg to 3 g, between about 75 mg to 2 g, between about 100 mg to 1.5 g, between about 100 mg to 1 g, between about 100 mg to 750 mg, between about 100 mg to 500 mg, between about 100 mg to 400 mg, between about 100 mg to 300 mg, between about 500 mg to 2 g, between about 500 mg to 3 g, between about 500 mg to 4 g, between about 500 mg to 5 g, and between about 750 mg to 5 g. Moreover, in some embodiments, the composition may include one or more omega-3 fatty acids in amounts amount from between at least about 1%, 5%, 10%, 20%, 25%, 30%, 40%, 50%, 60%, 70%, 75%, 80%, 85%, 90%, or 95% by weight based on the total weight of the composition. For example, in specific embodiments, the composition includes a combination of DHA (e.g., about 200-400 mg) and EPA (e.g., about 100-150 mg) that comprises about 50-75% by weight based on the total weight of the composition.

In some embodiments, the composition may include one or more tocopherols and/or tocotrienols. These may be high gamma tocopherols and/or tocotrienols. Vitamin E exists in eight forms: four tocopherols and four tocotrienols. Mixed tocopherols and/or tocotrienols refer to the combination of two or more compounds selected from the group costing of tocopherols and tocotrienols. Accordingly, the present composition can include one or more or mixed combination of these eight forms. The four tocopherols are alpha-tocopherol, beta-tocopherol, gamma-tocopherol, and delta-tocopherol. The four tocotrienols are alpha-tocotrienol, beta-tocotrienol, gamma-tocotrienol, and delta-tocotrienol. Some research suggests that vitamin E can protect against brain cell damage, prevent cancer, and reduce cholesterol. Some forms of vitamin E can be synthetically produced, while other forms are naturally occurring in nature. For instance, vitamin E naturally occurs in palm oil, wheat germ oil, sunflower oil, safflower oil, nuts and nut oils, green leafy vegetables, avocados, annatto, and more. Accordingly, the one or more mixed tocopherols and/or tocotrienols included in the composition can be extracted from palm oil, wheat germ oil, sunflower oil, safflower oil, nuts and nut oils, annatto, green leafy vegetables, avocados, and/or other suitable natural sources. In other embodiments, the composition includes only one or more tocotrienols or one or more tocopherols. In still other embodiments, the composition includes any form of vitamin E.

In some embodiments, the composition may include one or more tocopherols and/or tocotrienols in amounts between about 0.1 mg to 1 g, between about 1 mg to 1 g, between about 2 mg to 1 g, between about 5 mg to 750 mg, between about 10 mg to 750 mg, between about 15 mg to 500 mg, between about 15 mg to 500 mg, between about 15 mg to 400 mg, between about 15 mg to 300 mg, between about 15 mg to 200 mg, between about 15 mg to 100 mg, between about 15 mg to 75 mg, between about 15 mg to 40 mg, and between about 20 mg to 30 mg. Moreover, in some embodiments, the composition may include one or more mixed tocopherols and/or tocotrienols in amounts amount from between at least about 1%, 5%, 10%, 15%, 20%, 25%, or 30% by weight based on the total weight of the composition. For example, in specific embodiments, the composition includes one or more tocopherols and/or tocotrienols weighing about 15 to 65 mg and which comprises about 3-12% by weight based on the total weight of the composition.

In combination with omega-3 fatty acids and essentials oils, one or more mixed tocopherols and/or tocotrienols can synergistically and unexpectedly improve the stability of the omega-3 fatty acids and the essential oils. Tocopherols may occur naturally in a variety of foods including rice bran, avocados, almonds, and wheat germ, and can be used to retard oxidative damage or rancidity in fatty acids and or vegetable fats caused by exposure to oxygen, heat, water, or light. This can be quantified via a peroxide value, a para-anisidine value, a TOTOX value, an aldehyde value, an iodine value, or levels of free fatty acids.

In some embodiments, the composition includes one or more essential oils. Essential oils are naturally occurring aromatic liquids found in the roots, stems, bark, seeds, resin, flowers, and other parts of plants. These oils are fat soluble, non-water-based phytochemicals that include volatile organic compounds. The chemistry of any particular essential oil can be very complex and may consist of hundreds of different and unique chemical compounds. In nature, these oils give plants their distinctive smells, provide protection against disease, and assist in pollination. When separated from their parent plant, essential oils in their pure form are translucent with colors ranging from clear to pink or blue.

Suitable essential oils that can be included in the composition, in accordance with some embodiments, include essential oils from one or more of the following plants, and their related plant species: ajowan, almond, allspice, aloe, ammi visnaga (khella), amyris, angelica, anise, apricot, arnica, avocado, copaiba, balsam, basil, bay laurel, benzoin, bergamot, bergaptene, birch, borage, boronia, buchu, cajeput, calalmus, calendula, camellia, cannabis, caraway, cardamom, carnation, carrot, cassia, castor, catnip, cedar, cedarwood, celery, chamomile (including blue chamomile, German chamomile, Moroccan chamomile, Moroccan wild chamomile, and Roman chamomile), champaca, cilantro, cinnamon, cistus, citronella, ciste, clary sage, clementine, clove, cocoa, coconut, combava petitgrain, coriander, cornmint, costus, cumin, cypress, davana, dill, dill weed, elemi, erideron (fleabane), eucalyptus, fennel, sweet fennel, fenugreek, fir, frankincense, galbanum, garlic, genet, geranium, ginger, ginsing, grapefruit, pink grapefruit, white grapefruit, grapeseed, hazelnut, helichrysum, hemp, honeysuckle, hyssop, immortelle, fragrant aster inula, Jamaican gold, jasmine, grandiflorum jasmine, jojoba, jobquille, juniper, lanolin, lantana camara, laurel nobilis, lavender, lemon, lemongrass, lime, litsea, litsea cubeba, lotus, macadamia, mace, mandarin, manuka, marigold, marjarom, massoia, melissa, mimosa, monarda, mugwort, musk, myrrh, myrtle, narcissus, neroli, niaouli, nutmeg, oakmoss, ocotea, olibanum, opopanax, orange, blood orange, sweet orange, oregano, orris, osmanthus, palm, palmarosa, paprika, parsley, patchouli, peanut, pecan, pennyroyal, pepper, black pepper, peppermint, petitgrain, white pine, pine, primrose, ravensara anisata, redberry, rose, rosehip, rosemary, rosewood, rue, sage, sandalwood, seabuckthorn, sesame, shea, spikenard, spruce, blue spruce, St. John's wort, styrax, tagetes, tangerine, tea tree, thuja, thyme, tuberose, valerian, vanilla, verbena, vetiver, violete, vitex, walnut, wintergreen, wormwood, yarrow, and ylang ylang.

In some embodiments, the one or more essential oils included in the composition are 100% pure and/or uncut essential oils. Moreover, these oils may be derived from organically grown plants and/or be distilled by steam distillation. Such oils may are occasionally referred to as being therapeutic-grade essential oils.

In some embodiments, the composition may include one or more essential oils in amounts between about 0.1 mg to 2 g, between about 1 mg to 2 g, between about 2 mg to 2 g, between about 5 mg to 1.75 g, between about 10 mg to 1.5 g, between about 15 mg to 1.25 g, between about 15 mg to 1 g, between about 15 mg to 750 mg, between about 15 mg to 500 mg, between about 15 mg to 400 mg, between about 15 mg to 300 mg, between about 15 mg to 200 mg, between about 15 mg to 100 mg, between about 25 mg to 75 mg, between about 20 mg to 1 g, between about 20 mg to 1.5 g, and between about 20 mg to 2 g. Moreover, in some embodiments, the composition may include one or more essential oils in amounts amount from between at least about 1%, 5%, 10%, 15%, 20%, 25%, 30%, or 35% by weight based on the total weight of the composition. For example, in specific embodiments, the composition includes one or more essential oils weighing about 25 to 75 mg and which comprises about 5 to 15% by weight based on the total weight of the composition.

In some embodiments, one or more essential oils can improve the stability of omega-3 fatty acids and/or products containing such. For example, one or more essential oils can improve the stability of fish oil, while promoting freshness and reducing the occurrence of lipid oxidation. This improvement may be particularly prominent when the one or more essential oils contain greater than 10% by weight of phenylpropanoids (i.e., Eugenol, myristicin) or aromatic and/or phenol compounds with hydroxyl functional groups (i.e., thymol, carvacrol, cinnamaldehyde). Accordingly, the one or more essential oils included in the composition can contain greater than 10% of phenylpropanoids or aromatic and/or phenol compounds with hydroxyl functional groups. For example, the one or more essential oils can include clove, oregano, thyme, nutmeg, cinnamon, and mountain savory.

Oils such as German chamomile, without such hydroxyl or phenlypropanoid content, can also synergistically and unexpectedly contribute to the stability of the fish oil and help recycle vitamin E, because they possess elevated antioxidant activity as measured by ORAC, or Oxygen Radical Absorbance Capacity, a method that uses Trolox and Trolox Equivalence as a way of measuring the potential to absorb free radicals caused by oxidative damage.

As mentioned, embodiments of the composition can include vitamin D2 (ergocalciferol) and/or vitamin D3 (cholecalciferol). Vitamin D is a group of fat-soluble secosteroids responsible for intestinal absorption of calcium and phosphate. In some embodiments, the composition may include one or more of vitamin D2 and/or D3 in amounts between about 10 IU to 10,000 IU, between about 50 IU to 7,500 IU, between about 50 IU to 6,000 IU, between about 100 IU to 5,000 IU, between about 750 IU to 4,000 IU, between about 1,000 IU to 4,000 IU, between about 1,500 IU to 4,000 IU, between about 1,500 IU to 5,000 IU, between about 1,500 IU to 7,500 IU, and between about 1,500 IU to 10,000 IU. Moreover, in some embodiments, the composition may include one or more of vitamin D2 and/or D3 in amounts amount from between at least about 0.01%, 0.1%, 0.5%, 1%, and 2% by weight based on the total weight of the composition. For example, in specific embodiments, the composition one or more of vitamin D2 and/or D3 weighing about 200 to 300 IU and which comprises about 0.5% to about 2% by weight based on the total weight of the composition.

In some embodiments, the vitamin D2 and/or D3 ingredient may be included in the composition in a concentrated from. In these embodiments, the composition may include one or more of concentrated forms of vitamin D2 and/or D3 in amounts between about 1 IU to 1000 IU, between about 5 IU to 750 IU, between about 5 IU to 600 IU, between about 10 IU to 500 IU, between about 75 IU to 400 IU, between about 100 IU to 400 IU, between about 150 IU to 400 IU, between about 150 IU to 500 IU, between about 150 IU to 750 IU, and between about 150 IU to 1000 IU. Moreover, in some embodiments, the composition may include one or more of vitamin D2 and/or D3 in amounts amount from between at least about 0.001%, 0.005%, 0.01%, 0.02%, 0.03%, 0.04%, 0.05%, 0.075%, 0.1%, 0.15%, or 0.2% by weight based on the total weight of the composition. For example, in specific embodiments, the composition one or more of vitamin D2 and/or D3 weighing about 200 to 300 IU and which comprises about 0.05% to about 0.1% by weight based on the total weight of the composition.

As mentioned, embodiments of the composition can include coenzyme Q10 (CoQ10). When taken as a supplement by adults, CoQ10 may help normalize CoQ10 levels, which may decline in adulthood. CoQ10 may also assist in energy production and help maintain optimal cardiovascular and cognitive health. CoQ10 is also a powerful oil-soluble antioxidant that can synergistically retard oxidation of Omega-3s and enhance the activity of mixed tocopherols and tocotrienols. CoQ10 may be naturally found in fish or meat, soybean oil, olive oil, grapeseed oil, sunflower oil, argan oil, rice bran, and kaneka (yeast).

In some embodiments, the composition may include CoQ10 in amounts between about 0.1 mg to 900 mg, 0.1 mg to 500 mg, between about 1 mg to 500 mg, between about 2 mg to 500 mg, between about 3 mg to 400 mg, between about 3 mg to 300 mg, between about 3 mg to 200 mg, between about 3 mg to 100 mg, between about 3 mg to 75 mg, between about 3 mg to 50 mg, between about 5 mg to 50 mg, between about 5 mg to 25 mg, between about 5 mg to 100 mg, between about 5 mg to 300 mg, and between about 50 mg to 500 mg. Moreover, in some embodiments, the composition may include CoQ10 in amounts amount from between at least about 1%, 2%, 3%, 4%, 5%, 7.5%, 10%, 15%, or 20% by weight based on the total weight of the composition. For example, in specific embodiments, the composition includes CoQ10 weighing about 5 to 15 mg and which comprises about 1.5 to 4% by weight based on the total weight of the composition.

As mentioned, embodiments of the composition can include one or more carotenoids. The one or more carotenoids can include at least one or beta carotene, vitamin A, and/or analogues such as lutein, zeaxanthin, betacryptoxanthin, alpha carotene, astaxanthin and lycopene. In some embodiments, the composition may include one or more carotenoids in amounts between about 0.0001 mg to 1 mg, between about 0.0005 mg to 1 mg, and between about 0.001 mg to 0.1 mg. Moreover, in some embodiments, the composition may include one or more omega-3 fatty acids in amounts amount from between at least about 0.00001% to about 1. For example, in specific embodiments, the composition includes one or more carotenoids weighing about 0.0005 to 0.005 mg and which comprises about 0.002% to 0.003% by weight based on the total weight of the composition.

Additionally, the composition may include a capsule into which other components of the composition can be contained. In addition to being made of proteinaceous material from either porcine or bovine sources, this capsule can also be composed of fish protein or gelatin. In some embodiments, the capsule may include fish gelatin, with the fish gelatin comprising between 30-100% of the capsule. The capsule may also consist essentially of fish gelatin.

The following compositions represent several exemplary compositions contemplated by the present invention.

Composition One

| Ingredients | Percent by Weight |
|---|---|
| Omega-3 Fatty Acid(s) | 1-90% |
| Tocopherol(s)/Tocotrienol(s) | 1-18% |
| Essential Oil(s) | 1-30% |

Composition Two

| Ingredients | Percent by Weight |
|---|---|
| Omega-3 Fatty Acid(s) | 10-90% |
| Tocopherol(s)/Tocotrienol(s) | 1-18% |
| Essential Oil(s) | 1-30% |
| Fish gelatin | 5-30% |

Composition Three

| Ingredients | Percent by Weight |
|---|---|
| Omega-3 Fatty Acid(s) | 40-70% |
| Tocopherol(s)/Tocotrienol(s) | 3-10% |
| Essential Oil(s) | 5-20% |

Composition Four

| Ingredients | Percent by Weight |
|---|---|
| Omega-3 Fatty Acid(s) | 1-90% |
| Essential Oil(s) | 1-30% |
| Vitamin D2/D3 | 0.0001-2% |
| CoQ10 | 0.5-10% |

Composition Five

| Ingredients | Percent by Weight |
|---|---|
| Omega-3 Fatty Acid(s) | 1-90% |
| Essential Oil(s) | 1-30% |
| Vitamin D2/D3 | 0.0001-2% |
| CoQ10 | 0.5-10% |
| Fish gelatin | 1-30% |

Composition Six

| Ingredients | Percent by Weight |
|---|---|
| Omega-3 Fatty Acid(s) | 40-70% |
| Essential Oil(s) | 5-10% |
| Vitamin D2/D3 | 0.0001-2% |
| CoQ10 | 1-5% |

Composition Seven

| Ingredients | Percent by Weight |
|---|---|
| Omega-3 Fatty Acid(s) | 1-90% |
| Tocopherol(s)/Tocotrienol(s) | 1-18% |
| Essential Oil(s) | 1-30% |
| Vitamin D2/D3 | 0.0001-2% |
| CoQ10 | 0.5-10% |
| Carotenoids | 0.0002 |
| Fish gelatin | 10-30% |

Composition Eight

| Ingredients | Percent by Weight |
|---|---|
| Omega-3 Fatty Acid(s) | 1-90% |
| Tocopherol(s)/Tocotrienol(s) | 1-18% |
| Essential Oil(s) | 1-30% |
| Vitamin D2/D3 | 0.0001-2% |
| CoQ10 | 0.5-10% |

Composition Nine

| Ingredients | Percent by Weight |
|---|---|
| Omega-3 Fatty Acid(s) | 1-90% |
| Tocopherol(s)/Tocotrienol(s) | 1-18% |
| Essential Oil(s) | 1-30% |
| Vitamin D2/D3 | 0.0001-2% |
| CoQ10 | 0.5-10% |
| Carotenoids | 0.0002 |
| Fish gelatin | 10-30% |

Composition Ten

| Ingredients | Percent by Weight |
|---|---|
| Omega-3 Fatty Acid(s) | 40-70% |
| Tocopherol(s)/Tocotrienol(s) | 3-10% |
| Essential Oil(s) | 5-20% |
| Vitamin D2/D3 | 0.0001-2% |
| CoQ10 | 1-5% |

Composition Eleven

| Ingredients | Percent by Weight |
| --- | --- |
| Omega-3 Fatty Acid(s) | 40-70% |
| Tocopherol(s)/Tocotrienol(s) | 3-10% |
| Essential Oil(s) | 5-20% |
| Vitamin D2/D3 | 0.0001-2% |
| CoQ10 | 1-5% |
| Carotenoids | 0.00001-0.001% |
| Fish gelatin | 15-25% |

Although specific embodiments and applications of the invention have been described in this specification, these embodiments and applications are exemplary only, and many variations are possible.

We claim:

1. A dietary supplement composition comprising:
   omega-3 fatty acids in an amount between about 20 to 90 percent by weight;
   one or more of tocopherols and tocotrienols; and
   one or more essential oils in an amount of at least about 2 percent by weight.

2. The composition of claim 1, further comprising at least one of vitamin B2 and vitamin B3.

3. The composition of claim 2, further comprising coenzyme Q10 (CoQ10).

4. The composition of claim 1, further comprising coenzyme Q10 (CoQ10).

5. The composition of claim 1, wherein the one or more of tocopherols and tocotrienols are in an amount between about 3 to 15 percent by weight.

6. The composition of claim 1, wherein the omega-3-fatty acids are in the form of a marine or plant oil, wherein the one or more oils are cod liver oil, fish oil, flax oil, and krill oil.

7. The composition of claim 1, further comprising one or more carotenoid.

8. The composition of claim 1, wherein the one or more essential oils includes one or more of essential oil of clove, oregano, thyme, nutmeg, cinnamon, and mountain savory.

9. The composition of claim 1, wherein the one or more essential oils are present in at least an amount from about 5 percent by weight based on the total weight of the composition.

10. The composition of claim 1, wherein the one or more essential oils contain more than 10 percent by weight of phenylpropanoids and/or phenol compounds with hydroxyl functional groups.

11. A dietary supplement composition comprising:
    omega-3 fatty acids in an amount of at least 20 percent by weight;
    at least one of vitamin D2 and vitamin D3;
    coenzyme Q10 (CoQ10); and
    one or more essential oils in an amount of at least about 2 percent by weight.

12. The composition of claim 11, further comprising one or more of tocopherols and tocotrienols.

13. The composition of claim 12, wherein the one or more of tocopherols and tocotrienols are derived from palm oil.

14. The composition of claim 11, wherein the one or more omega-3-fatty acids comprises one or more of docosahexaenoic acid (DHA), eicosapentaenoic acid (EPA), and alpha-linolenic acid (ALA).

15. The composition of claim 11, further comprising one or more carotenoid.

16. The composition of claim 11, wherein the one or more essential oils includes one or more of essential oil of clove, oregano, thyme, nutmeg, cinnamon, and mountain savory.

17. The composition of claim 11, wherein the one or more essential oils are present in at least an amount from about 5 percent by weight based on the total weight of the composition.

18. The composition of claim 11, wherein the one or more essential oils contain more than 10 percent by weight of phenylpropanoids and/or phenol compounds with hydroxyl functional groups.

19. A dietary supplement composition comprising:
    omega-3 fatty acids in an amount of at least about 30 percent by weight; and
    a stabilizer for the omega-3 fatty acids, the stabilizer comprising:
    coenzyme Q10 (CoQ10);
    at least one of vitamin D2 and vitamin D3;
    one or more of tocopherols and tocotrienols; and
    one or more essential oils in an amount of at least about 2 percent by weight.

20. The composition of claim 19, wherein the one or more essential oils includes one or more of essential oil of clove, oregano, thyme, nutmeg, cinnamon, and mountain savory.

* * * * *